United States Patent [19]

Moore et al.

[11] Patent Number: 4,872,451
[45] Date of Patent: Oct. 10, 1989

[54] GLENOHUMERAL LIGAMENT REPAIR

[76] Inventors: Robert R. Moore, 1897 National Ave., Hayward, Calif. 94545; Steve Lamb, 6724 Corte Del Vista, Pleasanton, Calif. 94566; Eugene M. Wolf, 3400 California St., 2nd Floor, San Francisco, Calif. 94118

[21] Appl. No.: 9,667

[22] Filed: Feb. 2, 1987

[51] Int. Cl.[4] .............................................. A61F 5/04
[52] U.S. Cl. .............................. 128/92 YF; 128/92 V; 128/305
[58] Field of Search .......... 128/92 YF, 92 V, 92 VD, 128/92 YC, 305

[56] References Cited

U.S. PATENT DOCUMENTS

| | | | |
|---|---|---|---|
| 3,896,500 | 7/1975 | Rambert et al. | 128/92 YF |
| 4,278,091 | 7/1981 | Borzone | 128/92 YC |
| 4,462,395 | 7/1984 | Johnson | 128/92 YC |
| 4,573,448 | 3/1986 | Kambin | 128/92 V |
| 4,580,563 | 4/1986 | Gross | 128/92 YC |
| 4,590,928 | 5/1986 | Hunt et al. | 128/92 YF |
| 4,632,100 | 12/1986 | Somers et al. | 128/82 YF |
| 4,640,271 | 2/1987 | Lower | 128/92 YF |
| 4,653,486 | 3/1987 | Coker | 128/92 YF |

OTHER PUBLICATIONS

Markar Inc., Product Catalog, "New For 1986, Arthroscopic Products You Won't Find Anywhere Else", pp. 3, 6 (1986).

*Primary Examiner*—Dalton L. Truluck
*Attorney, Agent, or Firm*—Bielen and Peterson

[57] ABSTRACT

A ligament repair kit and procedure for installing a cannulated bone screw and ligament washer to retain ligament at a bone site using a first cannula in conjunction with selected obturators to engage and relocate ligament and in conjunction with a drill bit to drill a bone hole for anchoring, and using a second larger cannula with a driver to screw a bone screw into the bone hole retaining the relocated ligament at the anchoring site.

7 Claims, 2 Drawing Sheets

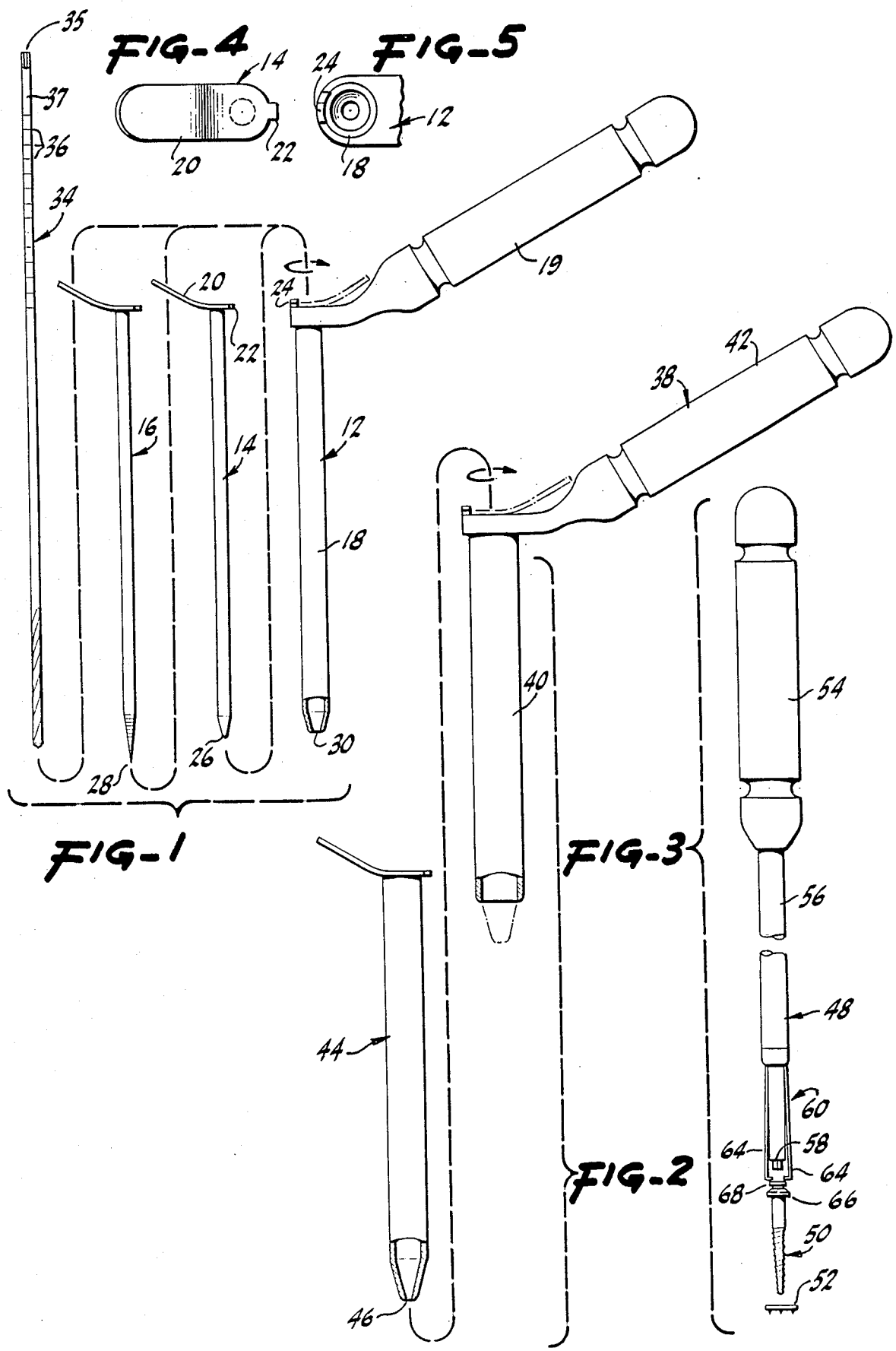

GLENOHUMERAL LIGAMENT REPAIR

BACKGROUND OF THE INVENTION

This invention relates to apparatus and procedures for the arthroscopic repair of torn shoulder ligaments. Arthroscopic procedures have greatly reduced the trauma of invasive surgery for internal structural repairs to ligaments and tendons. With the increase in the athletic activities of todays population, often without adequate training, a number of common injuries occur. The frequency of such injuries has warranted development of specialty procedures and instruments peculiar to a particular injury. Arthroscopic techniques once considered unusual and highly specialized, are currently being applied in a wide variety of situations for the diagnosis and treatment of injuries and diseases. The minimal surgical invasion to reach the site of repair or education with arthroscopic implements greatly reduces the physical trauma to the patient and the duration of healing.

In the repair of torn shoulder ligaments present techniques are less than wholly satisfactory. Currently, the repair of a torn glenohumeral ligament, which is a common cause of chronic repeated discloation of the shoulder, is accomplished by placing a staple in the glenoid area securing the ligament to the bone. Usually the procedure is an open procedure resulting in lengthy healing time and excessive scaring. Furthermore, the staples often bend, may undesirably loosen and may sometimes guillotine the ligament due to excessive pressure on setting.

Improved staple techniques have recently been developed that allow the stapling procedure to be performed arthroscopically as well as by open surgically. Using specially designed staples, a cannular provides an entry guide into the joint for insertion and initial setting of round staples with tapered staple limbs having reverse teeth to improve fixation. While this system resolves some of the problems, the imprecision of an impact setting system may result in severing the ligament or inadequately retaining the ligament against the bone.

The improved system described in this specification allows an arthroscopic repair to be accomplished with maximum assurance that the integrity of the repair will remain and that the trauma to the patient will be minimized.

SUMMARY OF THE INVENTION

The apparatus and procedures of this invention comprise an improved system for arthroscopic repair of torn shoulder ligaments. In particular, the repair system was devised to facilitate the repair of a torn glenohumeral ligament, a common cause of chronic, repeated dislocation of the shoulder. The instruments are usable in other reconstruction procedures where it is desirable to arthroscopically pin a ligament or tendon to a suitable bone anchoring site.

The instruments devised consist of two cannula with cannulated obturators, a graduated drill bit, a wrench and a cannulated screw with a spiked washer. The procedure is designed to prepare an anchoring site on the anterior scapular neck, seize and relocate anterior ligamentous structures to the prepared anchoring site where they are retained during drilling, and, pin the positioned ligamentous structures to the anchoring site with a screw.

These steps are performed using the specially designed instruments identified. The procedure minimizes the trauma to the patient, reduces the period of rehabilitation and limits the degree of scarring. A narrow cannular is used in conjunction with a blunt point obturator to penetrate an anterior portal to the glenohumeral ligament/labral complex. A trocar point obturator is then inserted in the cannula to spear anterior ligmentous structures and advance them to a previously prepared site where they are held by the end rim of the cannula. The obturator is removed and the ligaments pierced with a bone drill which drills a controlled depth hole in the bone. With drill in place, a k-wire is inserted through the cannulated drill to retain the ligaments when the drill and narrow cannula are removed. A borad cannula and blunt-nose, cannulated obturator are installed over the k-wire to provide a guide channel for a screw when the obturator is removed. A cannulated screw and ligament washer are passed over the k-wire and guided by the cannula to the drilled hole where the screw is installed with a cannulated hex driver. The large guide cannula is removed and the access incision closed.

The instruments and proceedings are described in greater detail in the detailed description of the preferred embodiment.

BRIEF DESCRIPTION OF THE DRAWINGS

FIG. 1 is a composite elevational view of the narrow cannula and the series of component implements used in conjunction with the narrow cannula.

FIG. 2 is a composite elevational view of the borad cannula and the component cannulated obturator.

FIG. 3 is an exploded view partially in section of the cannulated hex driver and bone screw with washer.

FIG. 4 is a top plan view of the blunt point obturator showing a locking tab.

FIG. 5 is a top plan view of the narrow cannula sowing the locking ridge.

DETAILED DESCRIPTION OF THE PREFERRED EMBODIMENT

Figure 6:
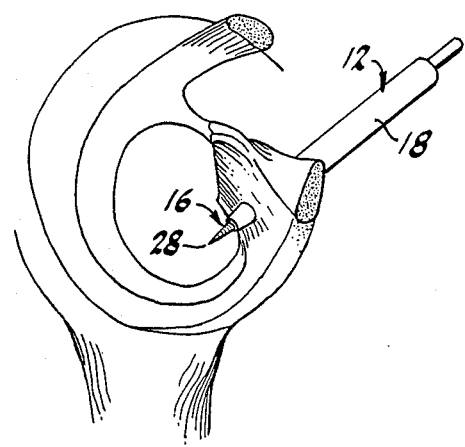
FIG. 6 is a schematic view of a step in the arthroscopic procedure showing the trocar point obturator relocating torn ligament.

Referring to the drawings, the implements comprising the glenohumeral ligament repair kit are shown in FIGS. 1-5 and the procedural steps are defined with reference to FIGS. 6-11. To first consider the implements, a 3.5 mm drill cannula 12 is shown in FIG. 1 in conjunction with a blunt point obturator 14 and a trocar point obturator 16. The drill cannula 12 has a slender barrel 18 and a connected handle 19. The obturators 14 and 16 are selectively inserted in the tubular barrel 18 of the cannular and locked in place on rotation of a lever 20 which engages a tab 22 on the cannula with a ridge 24 at the top end of the cannula barrel 18. The respective obturators each have a point 26, 28 which projects through an opening at the distal end 30 of the cannula barrel. The blunt point 26 permits the cannula to follow a prepared portal to the repair site. The trocar or sharp point 28 permits a ligament to be speared for relocation.

A cannulated drill bit 34 also shown in association with the slender 3.5 mm cannula in FIG. 1. The drill bit 34 is used to prepare a hole through relocated ligaments into an anchoring bone. The drill bit 34 has a central bore 35 and a series of graduations 36 on its shank 37. The drill bit 34 is used in conjunction with the cannula 12, which pins the ligaments to the bone and guides the drill. The depth of drilling is calculated using the graduations 36 and the entry top of the cannular barrel.

Referring to FIG. 2, a 9 mm drive cannula 38 with a broad or thick barrel 40 and handle 42 similar to that of the slender drill cannula is shown with an associated, conforming, blunt-nosed, cannulated obturator 44. The combined cannula 38 and obturator 44 replace the slender 3.5 mm cannula, which, after insertion of a retaining k-wire, is withdrawn from the access portal. The orifice 46 of the blunt nose obturator 44 is of sufficient size to allow the combined implement to be installed over the k-wire for insertion into the portal, guided by the k-wire.

An associated cannulated hex driver 48 and cannulated cortical bone screw 50 with its ligament washer 52 shown in FIG. 3 are sized for insertion into the 9 mm barrel 40 of the cannula 38 after the obturator 44 is withdrawn leaving the distal end of the barrel of the cannula and the k-wire to hold the ligaments in place.

The cannulated hex driver includes a handle 54 a shank 56 and a hex head 58 at the distal end of the shank which includes a clip 60 having two bent leaf springs 64. The bone screw 50 has a head 66 with a boss 68 that is engageable by the clip 60 on the driver to hold the screw in engagement with the driver during insertion or withdrawal of the screw from the repair site. The functions of the various features of the implements in the repair kit will become readily apparent from the following description of procedures for using the implements in a glenohumeral ligament repair. While the kit may be used for other ligament repairs it was developed in particular for repair of lesions of the glenohumeral ligament/labral complex using a bone screw and ligament washer instead of staples.

In this porcedure, an arthroscope is inserted through a posterior portal in the area of the glenoid for visualizing the glenohumeral ligaments and labrum. The damage to this complex is assessed and a plan is made for repair or stabilization. An incision is made in the anterior aspect of the shoulder providing a portal for an arthroscopic burr to abrade and denude the anterior scapular neck for a ligament anchoring site.

Figure 7:
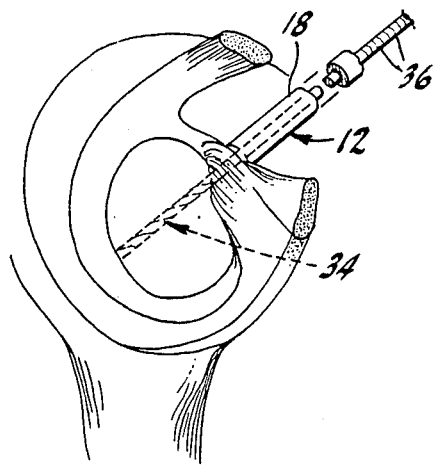
FIG. 7 is a schematic view in the procedure showing the bone drill.
Figure 8:
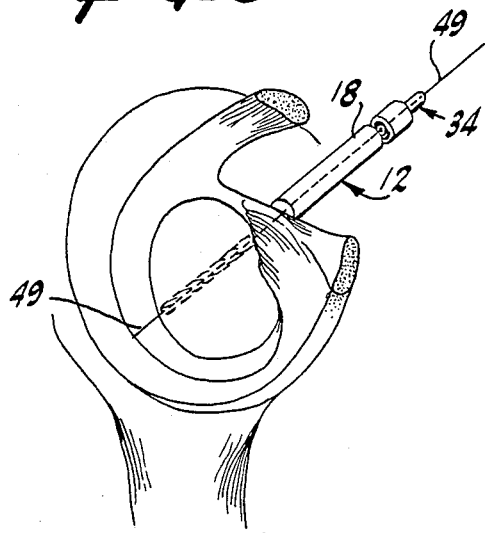
FIG. 8 is a schematic view in the procedure showing the K-wire inserted through the drill bit.
Figure 9:
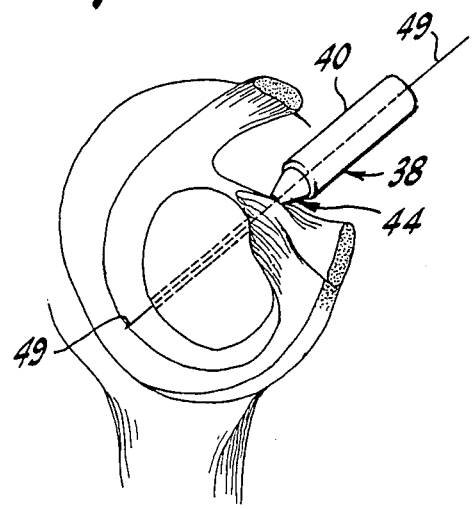
FIG. 9 is a schematic view in the procedure showing the borad cannula and obturator with the drill bit removed.

Using the slender 3.5 mm cannula 12 with the blunt point obturator 14, the cannular is inserted into the anterior portal to position the distal end of the cannula barrel proximate the anchoring site. The blunt point entry obturator 14 is replaced with the trocar point obturator 16 to spear anterior ligamentous structures and advance them to the abraded rim of the glenoid as shown in FIG. 6. The anterior glenohumeral ligament and labrum are transfixed and held in position by the end 30 of the cannula barrel 18. The trocar point obturator 16 is removed and the graduated drill bit 34 is used to drill into the scapular neck through the repositioned ligaments held by the cannula 12 as shown in FIG. 7. When the appropriate depth of the drill hole has been reached as measured by the graduations 36 on the drill bit for the particular length bone screw selected, then with the cannulated drill bit in place, a k-wire 49 is inserted through the drill bit 34 into the hole shown in FIG. 8. The drill bit 34 and the slender cannular 12 are sequentially withdrawn and the larger 9mm cannula 38 with the blunt nosed, cannulated obturator 44 are inserted over the k-wire 49 to the anchoring site as shown in FIG. 9. The obturator 44 is withdrawn and the end of the cannula assists the k-wire in seating the displaced ligaments on the anchoring site.

Figure 10:
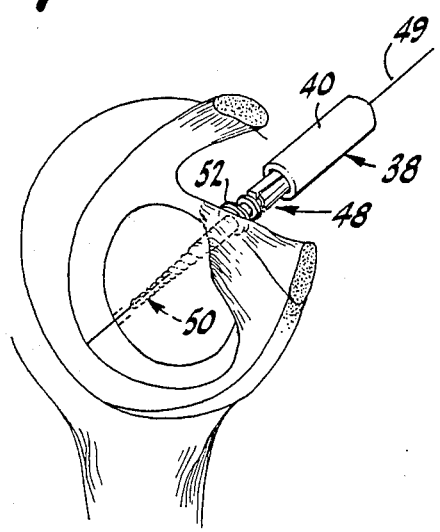
FIG. 10 is a schematic view in the procedure showing the bone screw and driver.
Figure 11:
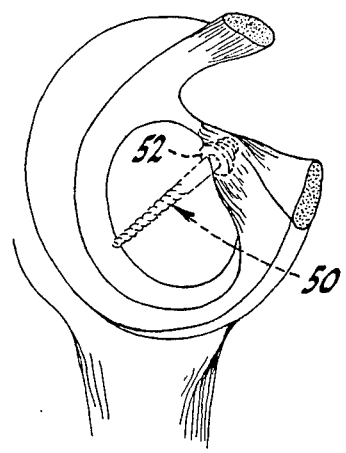
FIG. 11 is a schematic view in the procedure showing the screw.

Using the cannulated hex driver 48 the cannulated cortical bone screw 50 with its ligament washer 52 are inserted over the k-wire and into the cannula barrel to the drilled hole into which the screw is screwed to tighten the spiked ligament washer against the displaced ligaments to firmly hold them in place as shown in FIG. 10. The driver k-wire and cannula are withdrawn and the incision closed with the screw 50 in place as shown in FIG. 11.

While in the foregoing embodiments of the present invention have been set forth in considerable detail for the purposes of making a complete disclosure of the invention, it may be apparent to those of skill in the art that numerous changes may be made in such detail without departing from the spirit and principles of the invention.

What is claimed is:

1. A ligament repair kit for installing a ligament fastener comprising:
   a drill cannula having a slender tubular barrel with a distal end having an opening;
   at least one slender obturator having a pointed end sized and constructed to removably insert into the barrel of the drill cannula with the pointed end projecting through the opening at the distal end of the barrel, the drill cannula and inserted pointed obturator being constructed and adapted to spear ligamentous structures and advance them to an anchoring site;
   a cannulated drill bit having a central bore hole sized to fit over a conventional k-wire, the drill bit being sized to fit within the drill cannula and project through the distal end opening when the slender obturator is removed, the drill bit being connectable to a bone drill for drilling a bone hole while the drill cannula retains ligamentous structures over the anchoring site;
   a drive cannula having a tubular barrel with a distal end having an opening;
   a cannulated obturator constructed to removably insert in the tubular barrel of the drive cannula the cannulated obturator having a pointed tip and a narrow central bore hole sized to fit over a conventional k-wire installed through the cannulated drill bit to retain ligamentous structures at the anchoring site when the drill bit is removed; and
   a cannulated fastener driver having a shank with a bore hole sized to fit over a conventional k-wire, the shank having a driver tip with means for engaging a cannulated bone fastener wherein the shank and tip of the driver and the fastener are sized to fit within the barrel of the drive cannula over a conventional k-wire when the cannulated obturator is removed for installing the fastener into a hole drilled into an anchoring bone for retaining ligamentous structures at the anchoring site by the fastener.

2. The ligament repair kit of claim 1 wherein the fastener comprises a cannulated bone screw with a head having a projecting boss engageable with the sip of the driver and a ligament washer.

3. The ligament repair kit of claim 2 wherein the means for engaging the head of the screw comprises a hex head on the driver tip engageable with a conforming hex socket in the head of the bone screw.

4. The ligament repair kit of claim 1 having first and second slender obturators, the first with a blunt point end and the second with a trocar point end, the first slender obturator being constructed to aid in insertion of the drill cannula into a body portal and the second slender obturator being constructed to aid in engaging and relocating ligamentous structures.

5. The ligament repair kit of claim 1 wherein the drive cannula has a handle connected to the tubular barrel.

6. The ligament repair kit of claim 5 wherein the handle is detachable from the drive cannula.

7. A glenohumeral ligament repair procedure comprising the steps of:
   a. providing an portal to the anterior scapulas neck;
   b. abrading and denuding an anchoring site on the anterior scapular neck;
   c. positioning a drill cannular with a projecting slender, pointed obturator proximal to the anchoring site on the scapulas neck;
   d. engaging and relocating ligaments to the anchoring site with the drill cannular and projecting obturator by spearing the ligaments with the pointed obturator and displacing the speared ligaments to the anchoring site;
   e. removing the pointed obturator and holding relocated ligaments at the anchoring site with the drill cannula and while holding relocated ligaments with the drill cannula drilling a bone hole in the scapulas neck with a cannulated drill bit;
   f. while the drill bit is in place, inserting a k-wire into the bone hole through the cannulated drill bit;
   g. withdrawing the drill bit and drill cannula with the k-wire in place, retaining the ligaments;
   h. positioning a drive cannula and cannulated obturator over the k-wire;
   i. removing the cannulated obturator;
   j. inserting a cannulated fastener into the drive cannula over the k-wire;
   k. driving the fastener into the bone hole with a driver, capturing the ligament under the fastener; and
   l. removing the driver, drive cannula and k-wire and closing the access portal.

* * * * *